United States Patent
McEwan

(10) Patent No.: US 7,963,989 B2
(45) Date of Patent: Jun. 21, 2011

(54) IMPLANTABLE PROSTHETIC DEVICE FOR CONNECTION TO A FLUID FLOW PATHWAY OF A PATIENT

(75) Inventor: John Arthur McEwan, Dulles, VA (US)

(73) Assignee: Technology Advancement Group, Inc., Dulles, VA (US)

( * ) Notice: Subject to any disclaimer, the term of this patent is extended or adjusted under 35 U.S.C. 154(b) by 413 days.

(21) Appl. No.: 11/039,835

(22) Filed: Jan. 24, 2005

(65) Prior Publication Data

US 2006/0167539 A1    Jul. 27, 2006

(51) Int. Cl.
*A61F 2/06* (2006.01)

(52) U.S. Cl. ....................................................... 623/1.35

(58) Field of Classification Search .................. 606/200, 606/151, 152, 153; 623/1.35, 1.23, 1.13, 623/1.16, 1.32, 1.24; 600/504, 505
See application file for complete search history.

(56) References Cited

U.S. PATENT DOCUMENTS

| | | |
|---|---|---|
| 5,197,976 A | 3/1993 | Herweck et al. |
| 5,370,681 A | 12/1994 | Herweck et al. |
| 5,800,525 A * | 9/1998 | Bachinski et al. ............ 606/200 |
| 5,967,986 A * | 10/1999 | Cimochowski et al. ....... 600/454 |
| 6,110,201 A * | 8/2000 | Quijano et al. ................ 623/2.1 |
| 6,168,579 B1 | 1/2001 | Tsugita |
| 6,428,559 B1 | 8/2002 | Johnson |
| 6,585,756 B1 * | 7/2003 | Strecker ....................... 623/1.16 |
| 7,022,134 B1 * | 4/2006 | Quijano et al. .............. 623/1.24 |
| 7,226,476 B2 * | 6/2007 | Coppi ........................... 623/1.27 |
| 7,229,472 B2 * | 6/2007 | DePalma et al. ............. 623/1.16 |
| 7,261,733 B1 * | 8/2007 | Brown et al. ................. 623/1.34 |
| 2003/0114923 A1 * | 6/2003 | Swanick et al. ............. 623/1.35 |
| 2003/0120330 A1 * | 6/2003 | Ouriel et al. ................. 623/1.12 |
| 2004/0210250 A1 * | 10/2004 | Eskuri ............................ 606/200 |
| 2005/0049692 A1 * | 3/2005 | Numamoto et al. ......... 623/1.24 |
| 2005/0267322 A1 * | 12/2005 | LaRose ........................... 600/16 |

FOREIGN PATENT DOCUMENTS

WO    WO 2005/004752    *    1/2005

* cited by examiner

*Primary Examiner* — (Jackie) Tan-Uyen T Ho
*Assistant Examiner* — Dianne Dornbusch
(74) *Attorney, Agent, or Firm* — Nixon Peabody LLP

(57) ABSTRACT

An implantable prosthetic for connection to a fluid flow pathway of a patient. The prosthetic is comprised of a primary tube structure which is in communication with a plurality of secondary tube structures each of which contains filters for trapping embolic particles, such as blood clots, air bubbles, thrombus. etc. within a fluid flow pathway within a patient. The prosthetic also contains a monitoring device to non-invasively the flow of fluids through a patient's fluid flow pathway.

14 Claims, 4 Drawing Sheets

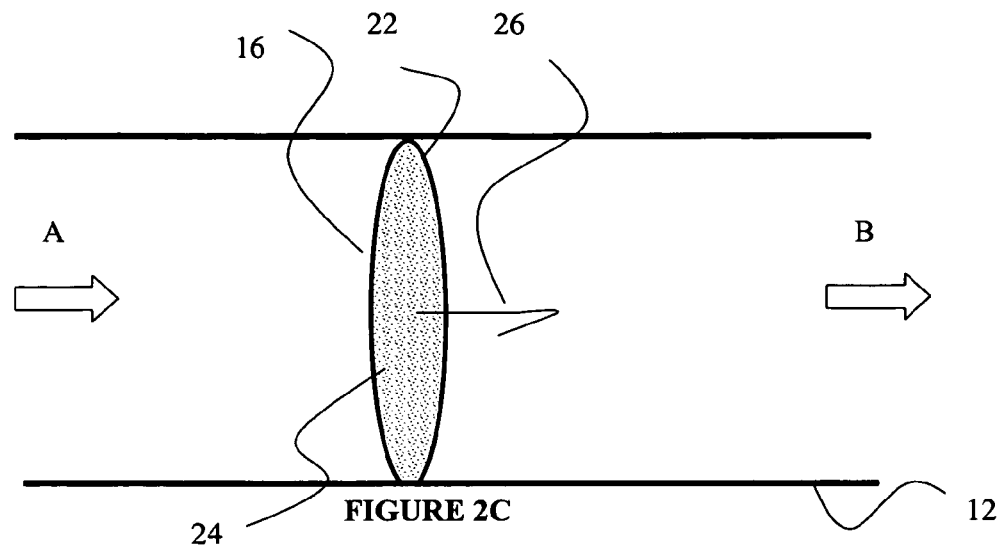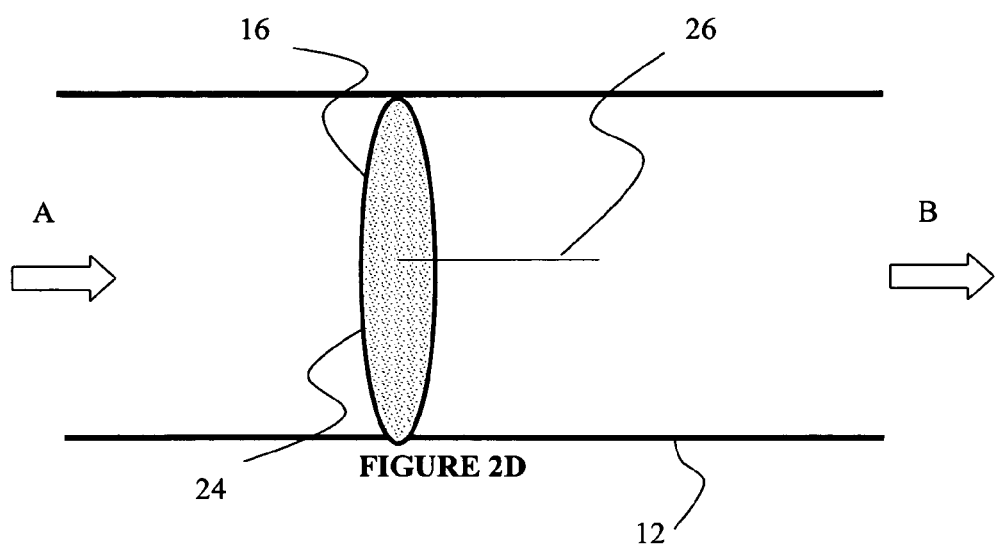

IMPLANTABLE PROSTHETIC DEVICE FOR CONNECTION TO A FLUID FLOW PATHWAY OF A PATIENT

BACKGROUND OF THE INVENTION

1. Field of the Invention

This invention relates to a implantable prosthetic device for connection to the fluid flow pathway of a patient, and more particularly to a implantable prosthetic device containing a plurality of tube structures having a filter for trapping objects such as embolic particles.

2. Discussion of Related Art

Increasing numbers and types of intralumenal procedures are being performed on medical patients. For example, there are intravascular blood flow measurement procedures, intravascular atherectomy procedures, intravascular drug therapy procedures, balloon angioplasty procedures, intravascular stent installation procedures, and even intravascular coronary bypass procedures (see, for example, U.S. Pat. No. 5,976,178 to Goldsteen, et al. which is herein incorporated by reference in its entirety). A concern commonly encountered in all these techniques is the accidental release of portions of the clots, plague, thrombus, debris, gas bubbles, or other embolic particulates, resulting in emboli which can lodge elsewhere in the vascular system. The creation and release of embolic particles can also occur spontaneously, absent medical intervention, especially in patients with blood-clotting disorders, such as phlebitis. Such emboli may be extremely dangerous to the patient, and may result in myocardial infarction, stroke, or limb ischemia.

Various devices have been developed to decrease the risk of embolism in patients during such procedures or suffering from such medical conditions. For example, U.S. Pat. No. 5,800,525 to Bachinski, et al. discloses a single bodily fluid filter with an elastic tubular framework that can be installed intralumenally to trap embolic particles in a bodily fluid conduit. However, since this device consists of a single filter, it does not provide for an alternative fluid flow path in the event that the filter becomes clogged.

U.S. Pat. No. 6,168,579 to Tsugita discloses a guidewire insertable within a guiding catheter which allows for the temporary placement of a filter in an artery or vein to capture atherosclerotic plaques and/or thrombi to capture embolic particles generated during endovascular procedures. This device, however, is designed only to capture embolic particles dislodged during the course of medical procedures and cannot be surgically implanted into a fluid flow pathway for long-term protection against naturally occurring embolic particles.

U.S. Pat. No. 5,370,681 Herweck et al. discloses a polyumenal implantable organ for sustained release of a bioactive material into a fluid flow pathway of a patient. The device comprises a body which defines a multiplicity of capillary lumina and is adapted for connection to the patient's fluid flow pathway to establish fluid flow through the capillary lumina. By seeding selected lumina of the device with a bioactive material, such as a therapeutic agent, diagnostic agent, etc. for contact with the body fluid, such as blood, the fluid can be treated as it passes through the device. This device does not provide a means by which embolic particles are filtered within the fluid flow pathway, and thus, does not serve to decrease a patient's risk of stroke, pulmonary embolism or other potentially deadly medical condition.

U.S. Pat. No. 5,197,976 to Herweck et al. discloses a vascular prosthesis comprising a plurality of parallel tube structures which are attached to one another over at least a portion of their longitudinal axis to form a branched arterial or venous graft for capable of being implanted without the necessity of suturing two grafts together. The tube structures of this device, however, do not comprise filtering devices for capturing hazardous embolic particles within a patient's fluid flow pathway.

Obviously, there are still major disadvantages associated with the existing technology which must be overcome. Specifically, the present day technology fails to provide patients with long-term protection against the potentially fatal conditions that result from blocked fluid flow pathways, including stroke, pulmonary embolism, and ischemia. Until now, there have been no implantable prosthetic devices containing multiple fluid flow pathways and filtering mechanisms to ensure the adequacy of the fluid flow within a patient capable of overcoming this technological shortfall.

SUMMARY OF THE INVENTION

It is an object of the present invention to provide a device which decreases the instances of stroke, embolism, and other potentially harmful effects associated with the presence of foreign particles within the fluid flow pathway of a patient.

It is another object of the invention provide an implantable prosthetic device for connection to the fluid flow pathway of a patient that helps to maintain long-term adequate flow of fluids through fluid flow pathways by filtering foreign particles and providing a means for monitoring the blood flow through the device.

A first aspect of the invention is a primary tube structure having a proximal end, a distal end, and a wall, wherein the wall defines an interior lumen of predetermined diameter. The primary tube structure is furcated at a predefined position between the proximal end and distal end of the primary tube structure into a plurality of secondary tube structures. The secondary tube structures comprise a wall which defines an interior lumen of predetermined diameter. The interior lumen defined by the wall of the primary tube structure is in communication with the interior lumen defined by the secondary tube structures. The lumen of each of the tube structure contains a filter.

The primary tube structure and secondary tube structures have a biocompatible exterior surface and are preferably composed of polytetrafluoroethylene selected from the group consisting of expanded tetrafluoroethylene, stretched polytetrafluoroethylene, and stretched and expanded polytetrafluoroethylene. The primary tube structure and secondary tube structures may also consist of a copolymeric material.

The filter positioned within the secondary tube structures is comprised of a frame and a porous covering coupled to the frame such that the porous covering covers the space defined by the frame. The pore size of the porous covering is preferably about 20 to about 300 microns and composed of a flexible polymeric material such as polyurethane, polyethylene or a copolymer thereof capable of stretching to achieve the diameter of a fluid flow pathway. In a preferred embodiment, the filters may be removed from the secondary tube structures for cleaning or replacement. The primary tube structure may also include a fluid flow monitoring device to ensure the operability of the invention.

In a second aspect of the invention provided is a method for inserting the implantable prosthetic device as described into a predefined location within a patient by surgically exposing a predefined region for insertion of the implantable prosthetic device and securing the device within the predefined region.

In a third aspect of the invention provided is a method of non-invasively monitoring fluid flow through an implantable prosthetic connected to a fluid flow pathway of a patient. This method comprises the steps of locating an external anatomical area on a patient proximate the situs of an implantable prosthetic device implanted within a fluid flow pathway of the patient and detecting fluid flow through said implantable prosthetic device implanted within a patient's fluid flow pathway using a fluid flow monitoring device.

BRIEF DESCRIPTION OF THE DRAWINGS

FIG. 2C is a schematic illustration of another blood flow monitoring device comprising a thin wire filament in the presence of decreased blood flow;

FIG. 2D is a schematic illustration of the blood flow monitoring device of FIG. 2C in the presence of increased blood flow.

DETAILED DESCRIPTION OF THE PREFERRED EMBODIMENTS

Strokes result from a sudden loss of brain function caused by a blockage or rupture of a blood vessel to the brain and is often characterized by loss of muscular control, diminution or loss of sensation or consciousness, dizziness, slurred speech, or other symptoms that vary with the extent and severity of the damage to the brain. The implantable prosthetic device, the preferred embodiments of which are herein disclosed and described is designed to decrease the instances of strokes, and other embolic events, such as pulmonary embolisms and ischemia in a patient by providing multiple pathway for the flow of fluids within a patient and a non-invasive method of monitoring the continued proper function of the device.

Figure 1:
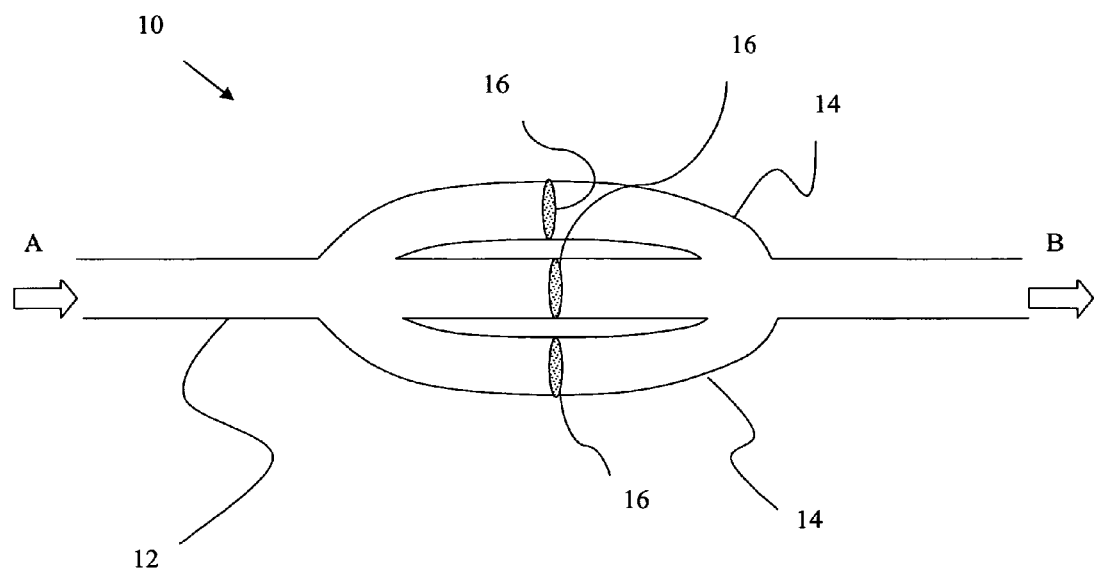
FIG. 1 is a schematic illustration of the an implantable prosthetic prosthesis.

In a first embodiment, an implantable vascular prosthesis for connection to the vascular pathway of a patient is provided as depicted in FIG. 1. Vascular prosthesis 10 includes a primary tube structure 12 defined by a proximal end A, a distal end B and a wall which separates the longitudinally exterior surface of primary tube structure 12 from the interior lumen. For purposes of describing the invention, it is herein assumed that when vascular prosthetic device 10 is implanted as described below, blood flows from the proximal end A of primary tube structure 12 towards the distal end B of primary structure 12, as shown by arrows in the accompanying figures. The wall of primary tube structure 12 defines a longitudinally exterior surface and an interior lumen of predetermined diameter. Primary tube structure 12 is furcated at a predefined position into a plurality of secondary tube structures 14, each of which is defined by a wall and interconnected to primary tube structure 12 such as to allow fluids to flow uninterruptedly from primary tube structure 12 into secondary tube structures 14. Note that the angles at which secondary tube structures interest with primary tube structures is illustrated as being exaggerated for clarity. Such angles preferably would be suitably set to avoid turbulent flow of blood. Each of secondary tube structures 14 houses a filter 16 operative to trap embolic particles, e.g., blood clots, thrombus, debris, gas bubbles, or other particles that could possibly cause a debilitating embolism, including a stroke within the patient. The term "furcated" as used herein refers to branching, dividing, joining, or other connections between primary tube structure 12 and plural secondary tube structures 14.

FIG. 2A-2D each illustrate filter 16 positioned within one of the of secondary tube structures 14. The filter in the other secondary tube structure can be similar. Filters 16 are preferably comprised of a frame 22 and a porous covering 24 coupled to frame 22 such that porous covering 24 covers the space defined by the frame. Frame 22 is preferably removably attached to the inside wall of secondary tube structures 14 such that entirety of filters 16 can be detached and removed from implantable vascular prosthesis 10 in the event it becomes clogged, dirty, or damaged, and needs to be cleaned or replaced.

In operation, the surgeon surgically exposes the desired region for introduction of vascular prosthesis 10. The desired site may be an area of occlusion or weakness in the patient's arteriovascular system, for example. An interruption of the patient's blood flow is performed in a known manner and vascular prosthesis is surgically implanted, sutured or otherwise secured in the desired location. Proper positioning of the prosthesis requires alignment of the lumen with the appropriate blood flow pathway such that the patient's blood flow is diverted through the lumen of primary tube structure 12. Once diverted into the lumen of primary tube structure 12 the blood is directed into one of the secondary tube structures containing filters 16. Any mobile embolic particles contained within the blood are trapped by filters 16, and the blood flow, now substantially devoid of embolic particles, continues in its course. If one of the of filters 16 become clogged, blood flow is continues through the another secondary tube structures 14 in an unhindered manner. Preferably, the cross-sectional area of the longer of each secondary tube structures 14 is equivalent to that of the lumen of primary tube structure 12. Accordingly, even a single fully clogged filter 16 will not substantially prohibit or limit normal blood flow. Filters 16 are designed such that they may be removed from secondary tube structures 14, if so desired, for cleaning, repair or replacement. Note the tube structures can be repaired or replaced. To do so, blood flow can be stopped through the appropriate structure, with a clamp or the like, and blood can flow through the other tube structures during the procedure without adversely affecting the patient.

Figure 2A:
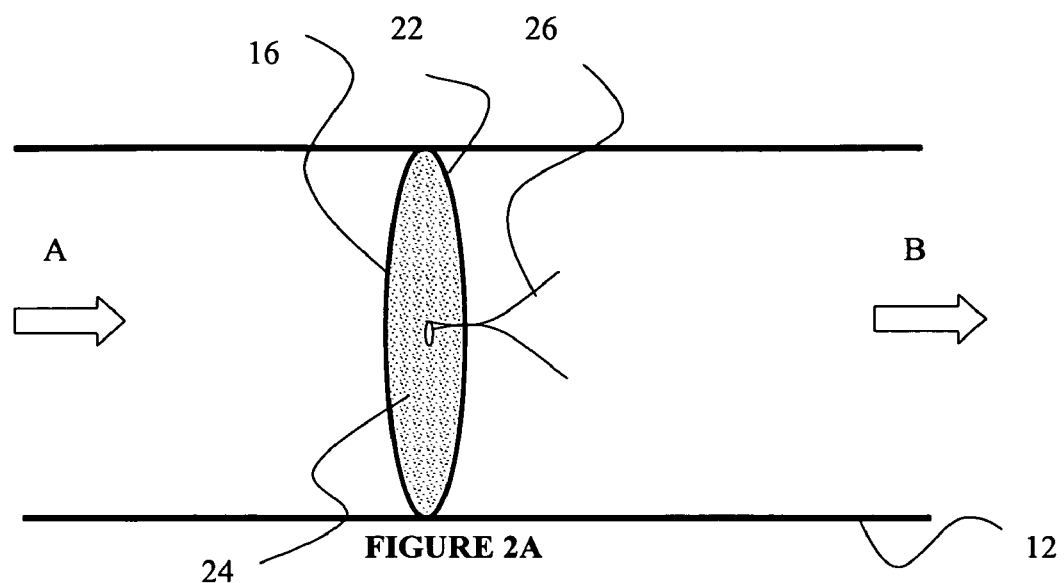
FIG. 2A is a schematic illustration of a blood flow monitoring device comprising a thin wire filament in the presence of decreased blood flow.
Figure 2B:
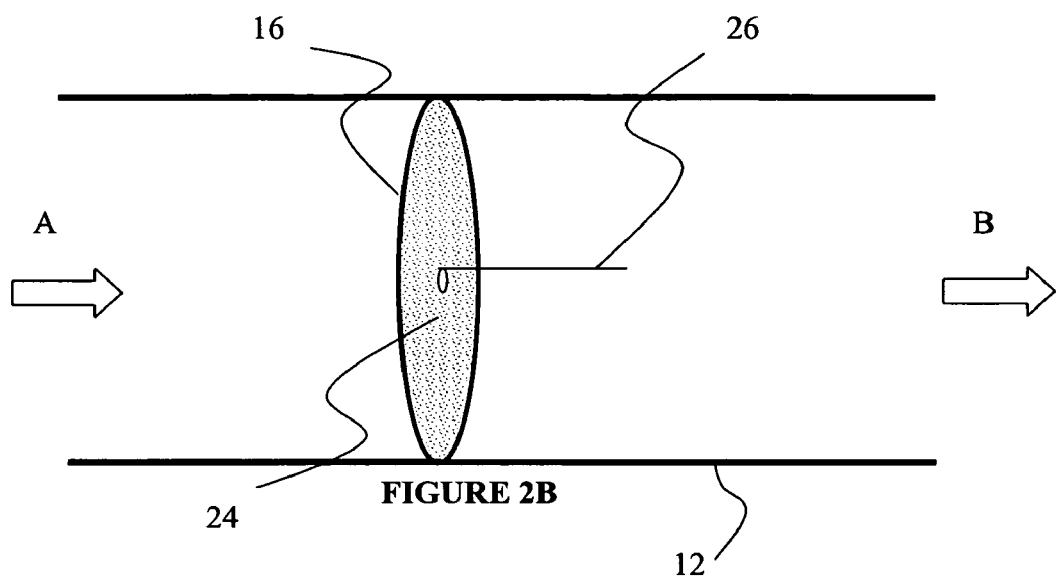
FIG. 2B is a schematic illustration of a blood flow monitoring device of FIG. 2A in the presence of increased blood flow.

Implantable vascular prosthesis 10 preferably comprises a device that indicates the blood flow through filters 16 which allows one to determine whether blood is passing through any one particular filters 16. The means by which the blood flow is measured is dependent on the type of device employed and may consist of devices which facilitate either visual and/or aural monitoring of a patients blood flow. FIG. 2A illustrates one such blood flow indicator which consists of a thin wire filament 26 consisting of at least two prongs. In its resting state, the two prongs of thin wire filament 26 are biased in opposite directions, as shown in FIG. 2A. When subjected to pressures created by blood flow, thin wire filaments 26 are forced together, as shown in FIG. 2B. Thin wire filament 26 is preferably coupled to the distal side of filters 16, such that when filter 16 is clogged by embolic particulates on its proximate side, the decrease in blood flow through filter 16 can be detected by visually observing the position of the two prongs of thin wire filament 26 in respect to one another using x-ray photography, magnetic resonance imaging or any other known imaging technique. A greater degree of separation between the two prongs of wire filament 26 indicates a corresponding decrease in blood flow in the associated secondary tube structures 14. By observing the position of thin wire film 26 associated with each secondary tube structures 14, one can determine which, if any, of filters are clogged or becoming clogged.

FIG. 2C illustrates another blood flow indicator which consists of a thin wire filament 26 that is normally curved. When subjected to pressures created by blood flow, thin wire filament 26 is straightened, as shown in FIG. 2D. Thin wire filament 26 is preferably coupled to the distal side of filters 16, such that when filter 16 is clogged by embolic particulates on its proximate side, the decrease in blood flow through filter 16 can be detected by visually observing the curve, or lack thereof using x-ray photography, magnetic resonance imaging or any other known imaging technique. A greater degree of curvature of filament 26 indicates a corresponding decrease in blood flow in the associated secondary tube structures 14. By observing the position of thin wire film 26 associated with each secondary tube structures 14, one can determine which, if any, of filters are clogged or becoming clogged.

Any imaging or sensing technique can be used to determine the status/position of the filaments. For example, x-ray imaging, magnetic resonance imaging or other imaging techniques can be used. Further, the blood flow indicator can have a detectable magnetic signature that permits blood flow detection using a magnetic induction or other magnetic sensor. Further RF sensors can be used.

Figure 3:
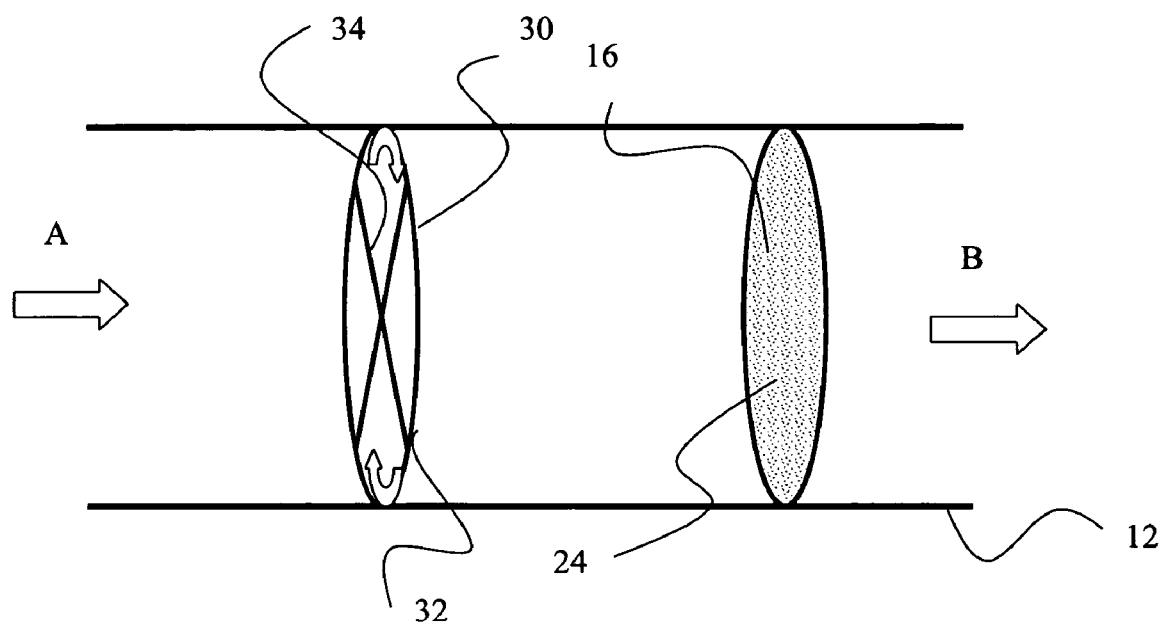
FIG. 3 is a schematic illustration of a blood flow monitoring device comprising a impeller.

FIG. 3 illustrates another blood flow indicator 30 comprising a frame 32 removably attached to the inside wall of secondary tube structures 14 and a impeller 34 which is rotatably attached to the inside of frame 32. Impeller 34 is set into either a clockwise or counterclockwise spin by the force of a patient's blood flow. The speed or relative degree of patient's blood flow can be determined by, for example, listening to audible signals created from the spinning of impeller 34. A weak audible signal indicates decreased blood flow, suggesting filter 16 associated with a secondary tube structures 14 may be clogged. A stronger, more audible signal indicates that the blood is flowing through filter 16 at a rate relative to the audible signal produced. As with filter 16, the blood flow indicator may be removed, if necessary, for cleaning, repair or replacement. The blood flow indicator may also be any known device for capable of emitting sounds corresponding to a given amount of blood flow within a fluid flow pathway. For instance, the blood flow indicator may consist of a valve or a plurality of valves, an impeller device, or any other known device capable of emitting specified sounds corresponding to a given amount of blood flow. Accordingly, depending on the type of blood flow indicator employed, any means of directly or indirectly monitoring blood flow can be used. For example, any type of imaging (e.g., x-ray photography, magnetic resonance imaging, etc.) audible sensing (e.g. stethoscope), magnetic induction sensing or other detection mechanism can be used to externally and non-invasively monitor the blood flow indicator. Further, the blood flow indicator can have a detectable magnetic signature that permits blood flow detection using a magnetic sensor. Further RF sensors can be used.

Note that in FIG. 3, impeller 34 is upstream, i.e. proximal, with respect to filter 16. This provides an added degree of safety. In the event that portions of impeller 34 break loose, they will be caught by filter 16 and not enter travel through the patients blood stream. However, impeller 34 can be positioned downstream of filter 34 if desired.

Primary tube structures 12 and secondary tube structures 16 can be manufactured from various biocompatible materials. For example, Teflon® brand polytetrafluoroethylene (PTFE), expanded tetrafluoroethylene, stretched polytetrafluoroethylene, and stretched and expanded polytetrafluoroethylene is suitable for use with the invention. Polymer alloys are suitable as well. Dacron® brand polyester fiber, mandrel spun polyurethane, and silicone elastomer fibers are also well suited for use with the invention. Copolymeric materials can also be utilized.

The internal diameter of the lumen of the primary tube structure and/or the secondary tube structures depends upon the intended use of each tube structure. In general, lumina having internal diameters of from about 3 mm to about 24 mm are useful as vascular grafts. For example, a tube structure intended for insertion in the arterial pathway can have a lumen internal diameter of from about 6 mm to about 18 mm. A tube structure for insertion in a venous pathway can have a lumen internal diameter from about 12 mm to about 24 mm. The outer diameter of the tube structures is generally not related to the internal lumen diameter. The thickness of the lumen walls will vary depending on the type of vascular graft. Generally, an arterial graft will require thicker walls than a venous graft. However, exact dimensions will depend on the specific purpose and environment in which the prosthetic device is employed.

Porous covering 24 may be made from any number of suitable materials, and is preferably made from a flexible polymeric material with elastomeric properties chosen from a group consisting of polyurethane, polyethylene or a co-polymer thereof. Porous covering 24 may also comprise any number of and configuration of pores and preferably comprises regularly-spaced holes wherein the pore size is from about 20 microns to about 300 microns. However, the pore size can be any size suitable for the intended purpose and environment in which the filter is used. Further, any filter structures can be used.

The invention may be embodied in other specific forms without departing from the spirit or essential characteristics thereof. For example, the implantable prosthetic device as disclosed as the preferred embodiments is not limited to use in the vascular system, but may also be employed in other fluid flow pathways, as well, including those within a patient's gastrointestinal system. The present embodiments are therefore to be considered in all respects as illustrative and not restrictive, the scope of the invention being indicated by the appended claims rather than the foregoing description, and all changes which come within the meaning and range of equivalency of the claim are therefore intended to be embraced therein.

What is claimed is:

1. An implantable prosthetic device for connection to the fluid flow pathway of a patient, comprising:
a fluid flow structure having a proximal end, a distal end, a first section, a second section, and a third section, said first section extending from said proximal end to a first position between said proximal end and said distal end, said third section extending from a second position between said first position and said distal end, and said second section extending between said first position and said second position, said first section and said third section only including a single interior lumen, said single interior lumen of said first section having a first cross-sectional area,
wherein said second section includes a plurality of interior lumens, said single interior lumen of said first and third sections being in communication with each of said plurality of interior lumens of said second section, said single interior lumen of said first section being furcated at said first position to form said plurality of interior lumens of said second section, said plurality of interior lumens of said second section combining at said second position to form said single interior lumen of said third section, each of said plurality of interior lumens having a second cross-sectional area, said second cross-sectional area being substantially equivalent to said first cross-sectional area of said single interior lumen of said first section, said plurality of interior lumens of said second section and said single interior lumen of said third section only receiving fluid that flows through said single interior lumen of said first section; and a filter disposed in each of said plurality of interior lumens of said second section.

2. The implantable prosthetic device of claim 1, wherein said first, second, and third sections of said fluid flow structure have a biocompatible exterior surface.

3. The implantable prosthetic device of claim 1, wherein said first, second, and third sections of said fluid flow structures are formed from polytetrafluoroethylene.

4. The implantable prosthetic device of claim 3, wherein said polytetrafluoroethylene is selected from the group consisting of expanded tetrafluoroethylene, stretched polytetrafluoroethylene, and stretched and expanded polytetrafluoroethylene.

5. The implantable prosthetic device of claim 1, wherein said first, second, and third sections of said fluid flow structures are formed from copolymeric material.

6. The implantable prosthetic device of claim 1, wherein said filter is comprised of a frame and a porous covering coupled to said frame such that said porous covering covers the space defined by said frame.

7. The implantable prosthetic device of claim 6, wherein the pore size of said porous covering is about 20 to about 300 microns.

8. The implantable prosthetic device of claim 6, wherein the said porous covering is a flexible polymeric material comprising regularly-spaced holes therein.

9. The implantable prosthetic device of claim 8, wherein said flexible polymeric material is chosen from the group consisting of polyurethane, polyethylene or a copolymer thereof.

10. The implantable prosthetic device of claim 8, wherein said flexible polymeric material is an elastomeric material capable of stretching to achieve the diameter of a fluid flow pathway.

11. The implantable prosthetic device of claim 1, wherein said filter is removable.

12. An implantable prosthetic device for connection to the fluid flow pathway of a patient, comprising:

a fluid flow structure having a proximal end, a distal end, a first section, a second section, and a third section, said first section extending from said proximal end to a first position between said proximal end and said distal end, said third section extending from a second position between said first position and said distal end, and said second section extending between said first position and said second position, said first section and said third section only including a single interior lumen, wherein said second section includes a plurality of interior lumens, said single interior lumen of said first and third sections being in communication with each of said plurality of interior lumens of said second section, said single interior lumen of said first section being furcated at said first position to form said plurality of interior lumens of said second section, said plurality of interior lumens of said second section combining at said second position to form said single interior lumen of said third section, each of said plurality of interior lumens having a second cross-sectional area, said second cross-sectional area being substantially equivalent to said first cross-sectional area of said single interior lumen of said first section, said plurality of interior lumens of said second section and said single interior lumen of said third section only receiving fluid that flows through said single interior lumen of said first section, each of said plurality of interior lumens of said second section including at least one fluid flow indicator, said at least one fluid flow indicator operatively connected to indicate a fluid flow when subjected to a pressure created by said fluid flow; and a filter disposed in each of said plurality of interior lumens of said second section.

13. The implantable prosthetic device of claim 12, wherein said at least one fluid flow indicator is a thin wire filament.

14. The implantable prosthetic device of claim 12, wherein said at least one fluid flow indicator is an impeller.

* * * * *